United States Patent [19]

Glowa et al.

[11] Patent Number: 5,779,697
[45] Date of Patent: Jul. 14, 1998

[54] ARTHROSCOPIC CANNULA WITH FLUID SEALS

[75] Inventors: Michael P. Glowa; Phillip J. Berman, both of St. Petersburg, Fla.

[73] Assignee: Linvatec Corporation, Largo, Fla.

[21] Appl. No.: 864,182

[22] Filed: May 28, 1997

[51] Int. Cl.$^6$ ..................... A61B 17/34
[52] U.S. Cl. ............ 606/185; 604/167; 604/169; 604/164
[58] Field of Search ............. 606/185; 604/167, 604/169, 164

[56] References Cited

U.S. PATENT DOCUMENTS

| | | |
|---|---|---|
| 3,970,089 | 7/1976 | Salce . |
| 3,994,287 | 11/1976 | Turp et al. . |
| 4,000,739 | 1/1977 | Stevens . |
| 4,177,814 | 12/1979 | Knepshield et al. . |
| 4,240,411 | 12/1980 | Hosono . |
| 4,341,239 | 7/1982 | Atkinson . |
| 4,424,833 | 1/1984 | Spector et al. . |
| 4,430,081 | 2/1984 | Timmermans . |
| 4,434,810 | 3/1984 | Atkinson . |
| 4,436,519 | 3/1984 | O'Neill . |
| 4,447,237 | 5/1984 | Frisch et al. . |
| 4,473,067 | 9/1984 | Schiff . |
| 4,475,548 | 10/1984 | Muto . |
| 4,525,910 | 7/1985 | Boehmer . |
| 4,535,818 | 8/1985 | Duncan et al. . |
| 4,535,819 | 8/1985 | Atkinson et al. . |
| 4,566,493 | 1/1986 | Edwards et al. . |
| 4,610,665 | 9/1986 | Matsumoto et al. . |
| 4,610,674 | 9/1986 | Suzuki et al. . |
| 4,612,960 | 9/1986 | Edwards et al. . |
| 4,626,245 | 12/1986 | Weinstein . |
| 4,634,432 | 1/1987 | Kocak . |
| 4,649,904 | 3/1987 | Krauter et al. . |
| 4,653,477 | 3/1987 | Akui et al. . |
| 4,655,752 | 4/1987 | Honkanen et al. . |
| 4,673,393 | 6/1987 | Suzuki et al. . |
| 4,705,511 | 11/1987 | Kocak . |
| 4,715,360 | 12/1987 | Akui et al. . |
| 4,723,550 | 2/1988 | Bales et al. . |
| 4,765,588 | 8/1988 | Atkinson . |
| 4,795,426 | 1/1989 | Jones . |
| 4,798,594 | 1/1989 | Hillstead . |
| 4,809,679 | 3/1989 | Shimonaka et al. . |
| 4,827,973 | 5/1989 | Boehmer . |
| 4,842,591 | 6/1989 | Luther . |
| 4,857,062 | 8/1989 | Russell . |
| 4,874,377 | 10/1989 | Newgard et al. . |
| 4,874,378 | 10/1989 | Hillstead . |
| 4,895,565 | 1/1990 | Hillstead . |

(List continued on next page.)

FOREIGN PATENT DOCUMENTS

| | | |
|---|---|---|
| 0 051 718 | 3/1984 | European Pat. Off. . |
| 0 564 373 | 10/1993 | European Pat. Off. . |
| 0 716 862 | 12/1995 | European Pat. Off. . |
| 42 10 984 | 10/1993 | Germany . |
| 43 03 026 | 8/1994 | Germany . |
| 34-5482 | 4/1959 | Japan . |
| 47-18190 | 9/1972 | Japan . |
| 55-58168 | 4/1980 | Japan . |
| 56-5668 | 1/1981 | Japan . |
| 61-203043 | 12/1986 | Japan . |
| 1199498 | 7/1990 | United Kingdom . |

*Primary Examiner*—Michael Buiz
*Assistant Examiner*—Daphna Shai
*Attorney, Agent, or Firm*—Gene Warzecha

[57] ABSTRACT

An elongated arthroscopic cannula having proximal and distal elastomeric sealing means through which elongated surgical instruments may be inserted. The cannula seals maintain their effectiveness with and without instruments present within the cannula. The distal sealing means is a transverse linear slit supported around its perimeter by a racetrack-shaped reinforcing member to engage instruments inserted therethrough and to seal the proximal side of the linear slit from the distal side when no instrument is used. The proximal sealing means is a floating, circular aperture capable of being laterally moved and tilted in order to provide a sealing function around an instrument shaft whether or not the shaft is aligned with the axis of the cannula.

20 Claims, 9 Drawing Sheets

U.S. PATENT DOCUMENTS

| | | | |
|---|---|---|---|
| 4,909,798 | 3/1990 | Fleischhacker et al. | |
| 4,917,668 | 4/1990 | Haindl | |
| 4,929,235 | 5/1990 | Merry et al. | |
| 4,946,133 | 8/1990 | Johnson et al. | |
| 4,960,412 | 10/1990 | Fink | |
| 4,978,341 | 12/1990 | Niederhauser | |
| 5,000,745 | 3/1991 | Guest et al. | |
| 5,009,391 | 4/1991 | Steigerwald | |
| 5,041,095 | 8/1991 | Littrell | |
| 5,064,416 | 11/1991 | Newgard et al. | |
| 5,104,379 | 4/1992 | Nakamura et al. | |
| 5,112,308 | 5/1992 | Olsen et al. | |
| 5,114,408 | 5/1992 | Fleischhaker et al. | |
| 5,125,903 | 6/1992 | McLaughlin et al. | |
| 5,127,909 | 7/1992 | Shichman | |
| 5,154,701 | 10/1992 | Cheer et al. | |
| 5,195,980 | 3/1993 | Catlin | |
| 5,195,994 | 3/1993 | Dieringer | |
| 5,197,955 | 3/1993 | Stephens et al. | |
| 5,207,656 | 5/1993 | Kranys | |
| 5,232,450 | 8/1993 | Green et al. | |
| 5,242,412 | 9/1993 | Blake, III | |
| 5,242,413 | 9/1993 | Heiliger | |
| 5,251,873 | 10/1993 | Atkinson et al. | |
| 5,267,966 | 12/1993 | Paul | |
| 5,269,763 | 12/1993 | Boehmer et al. | |
| 5,273,545 | 12/1993 | Hunt et al. | |
| 5,282,790 | 2/1994 | Clement | |
| 5,300,033 | 4/1994 | Miller | |
| 5,330,437 | 7/1994 | Durman | |
| 5,350,362 | 9/1994 | Stouder, Jr. | |
| 5,350,364 | 9/1994 | Stephens et al. | |
| 5,354,280 | 10/1994 | Haber et al. | |
| 5,391,153 | 2/1995 | Haber et al. | |
| 5,391,154 | 2/1995 | Young | |
| 5,431,676 | 7/1995 | Dubrul et al. | |
| 5,437,646 | 8/1995 | Hunt et al. | |
| 5,441,486 | 8/1995 | Yoon | |
| 5,441,487 | 8/1995 | Vedder | 604/169 |
| 5,453,095 | 9/1995 | Davila et al. | |
| 5,453,097 | 9/1995 | Paradis | |
| 5,458,640 | 10/1995 | Gerrone | |
| 5,476,475 | 12/1995 | Gadberry | |
| 5,490,843 | 2/1996 | Hildwein et al. | |
| 5,492,304 | 2/1996 | Smith et al. | |
| 5,496,280 | 3/1996 | Vandenbroek et al. | |
| 5,496,289 | 3/1996 | Wenstrom, Jr. | |
| 5,514,098 | 5/1996 | Pfoslgraf et al. | |
| 5,514,109 | 5/1996 | Mollenauer et al. | |
| 5,520,663 | 5/1996 | Patterson et al. | |
| 5,542,931 | 8/1996 | Gravener et al. | |
| 5,545,142 | 8/1996 | Stephens et al. | 604/167 |
| 5,545,150 | 8/1996 | Danks et al. | |
| 5,554,124 | 9/1996 | Alvarado | |
| 5,562,632 | 10/1996 | Davila et al. | |
| 5,575,769 | 11/1996 | Vaillancourt | |
| 5,584,850 | 12/1996 | Hart et al. | |
| 5,603,702 | 2/1997 | Smith et al. | |
| 5,613,954 | 3/1997 | Nelson et al. | 604/167 |
| 5,628,732 | 5/1997 | Antoon, Jr. et al. | |
| 5,634,908 | 6/1997 | Loomas | |
| 5,657,963 | 8/1997 | Hinchliffe et al. | |
| 5,662,615 | 9/1997 | Blake, III | |

ARTHROSCOPIC CANNULA WITH FLUID SEALS

BACKGROUND OF THE INVENTION

1. Field of the Invention

The invention relates to a cannula for use in arthroscopic or endoscopic surgical procedures in which the cannula permits introduction of surgical instruments into a patient and wherein the cannula must be sealed to minimize uncontrolled loss of irrigating or other fluid from the surgical work site. More particularly, the invention relates to an arthroscopic cannula having fluid seals for sealing off the work site when elongated arthroscopic instruments are inserted through the cannula as well as when no instrument is present in the cannula.

2. Description of the Prior Art

Numerous devices exist to provide arthroscopic or endoscopic cannulas with seals to prevent the loss of irrigating or insufflating fluid from the surgical work site. While such cannulas are designed to overcome similar concerns in both laparoscopic (and other like) procedures utilizing pressurized gases to distend a body cavity and arthroscopic procedures utilizing pressurized liquids to distend and irrigate a joint or body cavity, the invention disclosed herein will be described in terms of an embodiment intended for arthroscopic procedures. It will be understood that the invention is adaptable to all endoscopic procedures in which a cannula is used.

Arthroscopic (or, more generally, endoscopic) surgical procedures enable closed surgery to be performed via portals through which a variety of elongated instruments may be passed to gain access to an internal surgical work site. Very often a disposable cannula is inserted into the portal in order to provide a convenient passageway through which various instruments may pass. Because many arthroscopic procedures require the use of pressurized fluid to distend and irrigate the joint being operated upon, the cannula must provide a sealed passageway in order to enable instruments to be passed into and out of the cannula while maintaining a fluid seal whether or not an instrument is in the cannula passageway. The sealing of such cannula passageways is usually accomplished by one or more elastomeric membranes attached to the proximal end of the elongated cannula and such cannulas are referred to herein as cannula seals or sealing cannulas. Prior art attempts at sealing have met with varying degrees of success, but improvements are desirable. Since differing considerations come into play at different times during the use of such cannulas, some prior art devices utilize two different sealing mechanisms: one optimized for sealing when no instrument is present in the cannula and another optimized for sealing while an instrument is present -hence the term "two-stage" is sometimes used to describe such cannulas.

The variety of instruments which must be inserted through the cannula seal includes instruments of varying sizes and configurations. While the instrument shafts are usually cylindrical, some instruments may have unusually large or sharp distal tips which may cut a seal element upon the insertion or extraction of the instrument thus making it less suitable for subsequent instruments which must be inserted during the same surgical procedure. It is desirable, therefore, to devise a sealing cannula which minimizes this problem.

One known cannula seal is described in U.S. Pat. No. 4,655,752 (Honkanen et al.) in which a pair of conically tapered seal members is disposed in the proximal end of a cannula. One of the seal members has a circular aperture at the small end of a tapered conical member and the other seal member has a transverse slit placed on the axis of a second conical member. The circular aperture enables a fluid seal to be maintained around an instrument shaft inserted through the cannula while the first seal member enables the fluid pressure within the joint to press the two lips of the seal together to maintain pressure when no instrument is present.

While somewhat better than many planar sealing elements, known conical seal structures such as this are sometimes affected by friction between an instrument shaft and the conical seal members on extraction, causing the conical seal members to become everted. This obviously compromises the seal's integrity and may sometimes require the seal to be manually repositioned before the next instrument can be inserted.

Other, more complex sealing systems are known. For example, in U.S. Pat. No. 5,603,702 (Smith et al) which describes a valve system in which a plurality of concentrically arranged, pivotable guard members is interposed between the instrument and a conical elastomeric seal. The intent is to assist the insertion of an instrument by minimizing the forces exerted by the instrument on the resilient seal member.

It is accordingly an object of this invention to produce a disposable sealing cannula which is able to maintain a fluid seal with or without an instrument present in the cannula passageway.

Since the fluid at the work site is pressurized, care must be taken to avoid leakage during the time the instrument is being inserted. Consequently, another object of this invention is to produce a sealing cannula capable of accommodating varying degrees of misalignment during instrument insertion.

It is also an object of this invention to produce a sealing cannula which minimizes the deformation (eversion) of an elastomeric member upon extraction of an instrument.

It is an additional object of this invention to produce a sealing cannula which minimizes any tendency for instruments to cut or destroy a seal element upon instrument insertion.

SUMMARY OF THE INVENTION

These and other objects of the invention are achieved by the preferred embodiment disclosed herein which is a sealing cannula for enabling passage of elongated instruments therethrough comprising a tubular housing having an axis, an inner surface and outer surface, a distal end, a proximal end and an axially aligned tubular body extending distally from the distal end. A first, proximal elastomeric seal is provided on the housing, this seal comprising a first tubular wall having a proximal end, a distal end and a first transverse end wall at the proximal end. The first transverse end wall comprises an expandable circular aperture supported by a floating means for enabling lateral and inclined motion of the circular aperture relative to the axis when an elongated instrument is inserted through the cannula. The first tubular wall is secured to the housing so as to align the circular aperture along the axis and space it a certain distance from the proximal end of the housing. A second, distal elastomeric seal is provided in the housing, this seal comprising a second tubular wall having a proximal end, a distal end and a second transverse end wall at the distal end. The second transverse end wall has proximal and distal sides, a transversely oriented linear slit therethrough and is secured within the housing so as to align the slit along the axis and space it a

3 certain distance from the circular aperture. A generally rectangular, primary reinforcing member is formed about the slit, and extends distally from the second transverse end wall on the distally facing side of the end wall. This reinforcing member is a racetrack-shaped, raised rib that has planar, inclined lead-in surfaces on either side of the slit to facilitate instrument insertion and removal.

The invention also resides in the method of sealing a cannula to enable sealing even during misalignment of the instrument relative to the axis of the cannula. The method comprises the steps of providing an elongated cannula body having a tubular passageway and providing at the proximal end of the body a distal seal for sealing the work site when no instrument is present in the cannula. The method also comprises the steps of providing a proximal seal for sealingly engaging an instrument shaft of an instrument inserted through the cannula and providing a floating means associated with this proximal seal for enabling it to move relative to the axis of the cannula to maintain engagement between the proximal seal and the instrument shaft within a predetermined range of misalignment of the axis of the instrument shaft with the axis of the cannula. The floating means is a relatively thin annular wall section that supports the proximal seal (e.g. an axially aligned, expandable circular aperture) at a predetermined distance from the proximal end of the cannula body.

4

DESCRIPTION OF THE PREFERRED EMBODIMENT

Referring to the drawings, an arthroscopic cannula 10 comprises an elongated hollow, cylindrical body portion 12 provided with a continuous external thread 14 between its proximal end 16 and its distal end 18. Tubular body 12 has an interior passageway 22 aligned along an axis 24 through which elongated endoscopic instruments may pass. An optional fluid inlet port 26 has an interior channel 28 which communicates with the interior passageway 22 of tubular body 12 in order to provide fluid inflow to the surgical work site. It will be understood that if this port is present, the fluid flows around any instrument shaft (not shown) which extends through the passageway. One or more optional fenestrations 20 may be provided at the distal end of the body to vary the fluid path. Channel 28 is provided with an enlarged transverse recess 31 which receives a stopcock valve 200 to be described in greater detail below. It will be understood that the cannula seal invention described herein may be used without fluid inlet 26.

Figure 1:
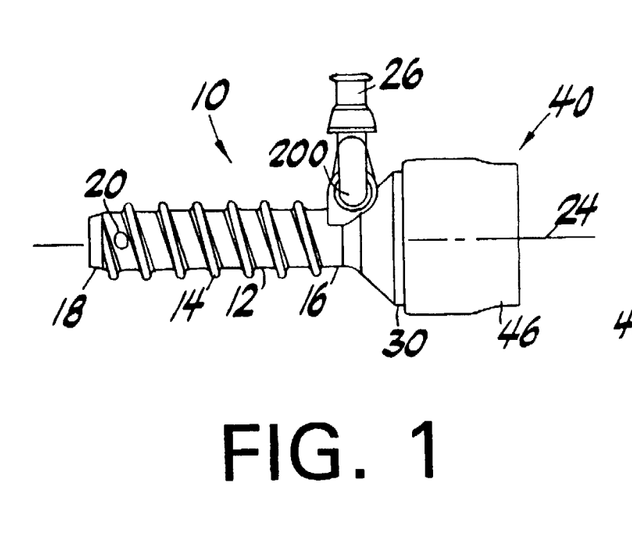
FIG. 1 is a side elevational view of an arthroscopic cannula constructed in accordance with the principles of this invention.
Figure 2:
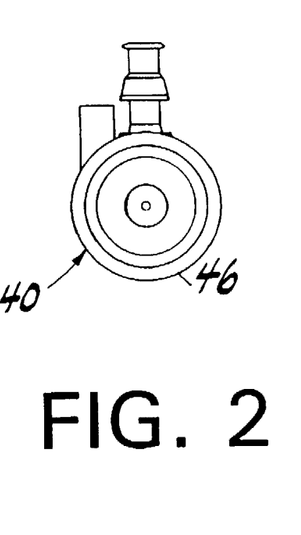
FIG. 2 is a right side view of FIG. 1.
Figure 3:
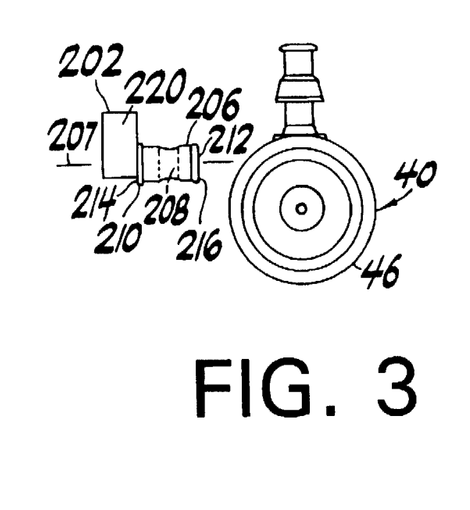
FIG. 3 is an exploded view of FIG. 2 showing a valve stem disengaged from the body of the cannula.

Integrally formed at the proximal end of tubular body 12 is a tubular housing 30 surrounding a chamber 32 aligned with axis 24. In the preferred embodiment housing 30 has cylindrical inner and outer surfaces provided with various annular grooves and ribs to facilitate the attachment of elastomeric valve assembly 40 at the proximal end of the housing. Valve assembly 40 comprises three individual components: an elastomeric inner or distal seal 42, a rigid intermediate reinforcing and limitation member 44 and an elastomeric outer or proximal seal 46. When assembled, the outer seal 46 will be stretched around the cylindrical housing 30 and may, therefore, adopt a deformed shape (shown in FIGS. 1 and 4) in which the diameter of its proximal end is smaller than the diameter of its distal end.

Inner seal 42 comprises an elastomeric body adapted to fit within housing chamber 32. In the preferred embodiment, since the housing is cylindrical, inner seal 42 has a cylindrical body 50 having a predetermined axial length L1, an annular groove 52 adjacent its proximal end and a linear slit 54 adjacent its distal end. Slit 54 has a length L2 in a direction transverse to axis 24 and is surrounded by a generally rectangular or racetrack (elongated oval) shaped primary reinforcing member 56. The reinforcing function of member 56 is bolstered by a pair of opposed, lateral (secondary) reinforcing members 58 and 60. Length L2 is relatively long in order to accommodate large diameter instrument shafts. In one preferred embodiment, distal seal 42 is molded from a biocompatible elastomeric material having a sufficient amount of flexibility, resilience and elongation range to accommodate a selected range of instrument shaft sizes (such as a range from 2.7 mm to 8.4 mm diameter). The overall maximum diameter D1 of body 50 is 0.9 inches (22.86 mm) and its longitudinal length L1 is 0.5 inches (12.70 mm). Slit length L2 may be on the order of 0.3 inches (7.62 mm) while dimensions D2 and D3 of member 56 may be on the order of 0.7 inches (17.78 mm) and 0.4 inches (10.16 mm), respectively.

Figure 6:
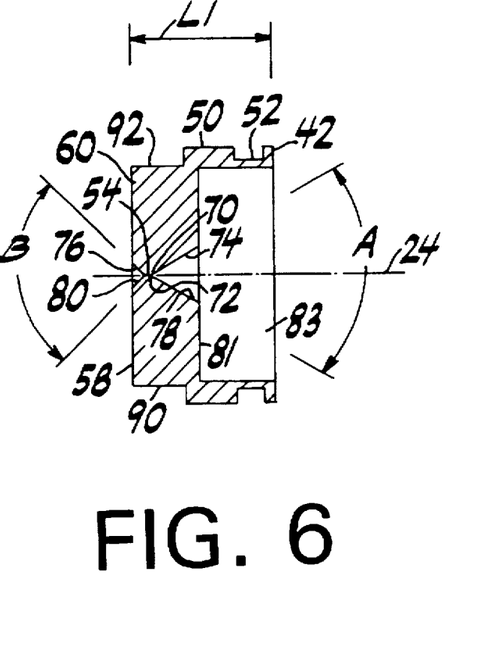
FIG. 6 is an isolated view of a portion of FIG. 5 showing the distal seal member of the present invention.
Figure 7:
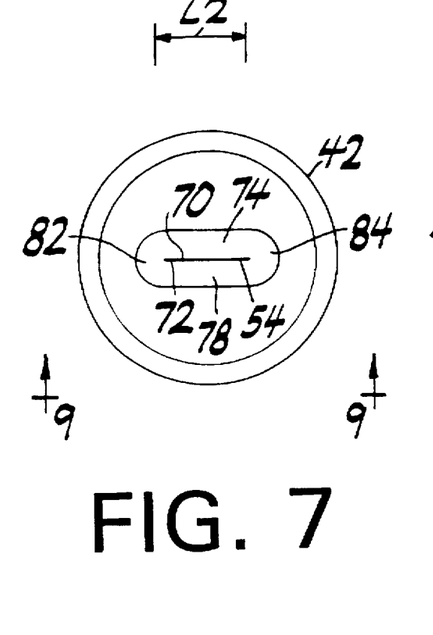
FIG. 7 is a right side view of FIG. 6.
Figure 8:
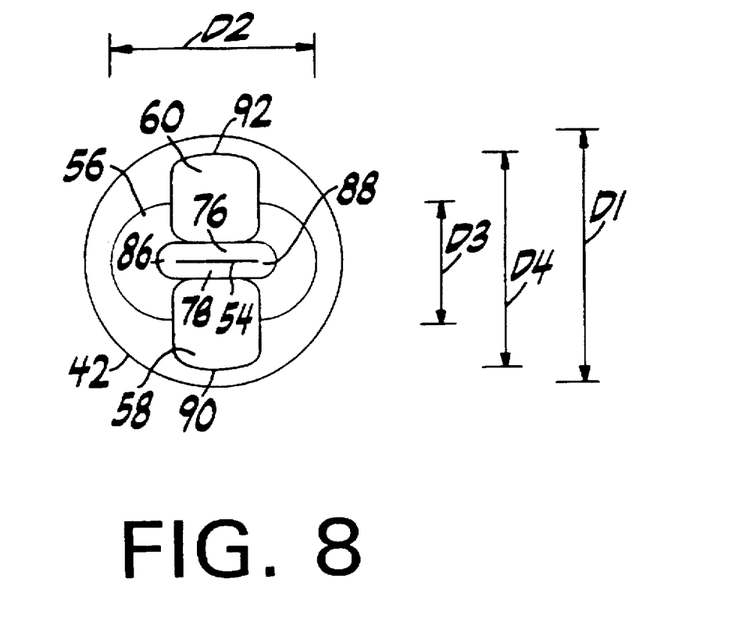
FIG. 8 is a left side view of FIG. 6.

The slit 54 is defined by a pair of opposing linear edges 70 and 72 defined by the intersection of a pair of planar lead-in surfaces. Thus, edge 70 is defined at the intersection of proximal lead-in surface 74 and distal lead-in surface 76 while edge 72 is defined at the intersection of proximal lead-in surface 78 and distal lead-in surface 80. In the preferred embodiment, edges 70, 72 are centered at a point spaced 0.063 inches (1.59 mm) from the distal surface of reinforcing member 56 and 0.175 inches (4.46 mm) from the proximal surface (i.e. the bottom or floor surface 81 of interior area 83). These edges 70, 72 may actually be joined during manufacture by a thin, frangible membrane which is then cut to form two facing surfaces having a longitudinal length (parallel to L1) on the order of 0.002 to 0.020 inches (0.05 mm to 0.51 mm). Manufacturing tolerances may result in edges 70, 72 which (when viewed as in FIG. 6) range from relative point contacts to contact between opposing flat faces. Proximal lead-in surfaces 74 and 78 are oriented at an angle A relative to each other while distal lead-in surfaces 76 and 80 are oriented at an angle B relative to each other. In the preferred embodiment these angles are on the order of 60° and 90°, respectively. As best seen in FIG. 7, proximal lead-in surfaces 74 and 78 are planar in a direction transverse to axis 24, parallel to slit 54, and are joined at their adjacent ends by opposing conical wall sections 82 and 84. The apex of each of these proximal conical wall sections coincides with the end of the slit adjacent a particular section so the surface of each planar section smoothly blends with the surfaces of the conical wall sections. Distal lead-in surfaces 76 and 78, as best seen in FIG. 8, are similarly joined at the their ends by opposing conical wall sections 86 and 88. The apex of these distal wall sections is also coincident with the ends of the slit. The term "lead-in" is used with respect to the proximally facing surfaces 74, 78 because these surfaces assist in positioning the tip of an instrument centrally, to facilitate its insertion through the cannula. Distally directed pressure on these surfaces (to the left in FIG. 4) by an instrument will urge slit 54 to open before the slit edges 70, 72 actually touch the instrument tip. This action minimizes any tendency for the instrument to tear the slit or hang-up on insertion. The term "lead-in" is also applied to the distally facing surfaces 76, 80 just for symmetry. These surfaces, however, serve to minimize surface contact between an instrument shaft and the area adjacent the slit, thereby assisting in the minimization of any tendency for seal eversion as instruments are retracted proximally. As will be understood below, the profile of the reinforcing members also helps prevent eversion.

Figure 9:
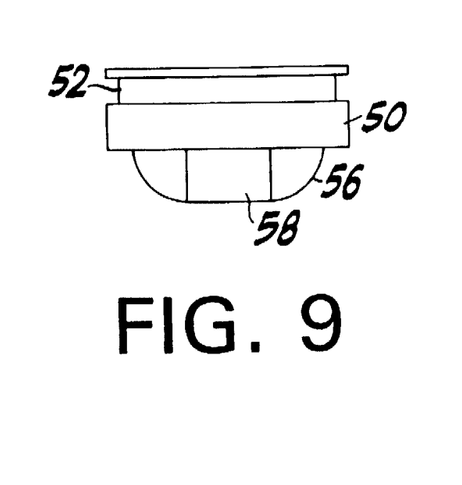
FIG. 9 is an elevational view of FIG. 7 taken along the line 9—9.
Figure 10:
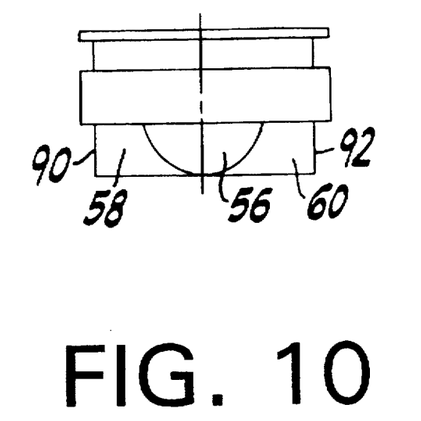
FIG. 10 is a right side view of FIG. 9.
Figure 11:
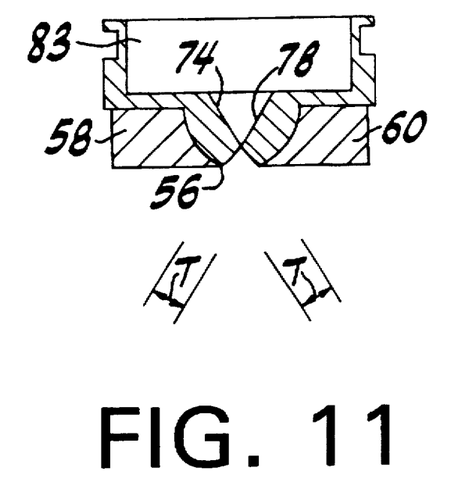
FIG. 11 is a cross-sectional view of FIG. 10.
Figure 12:
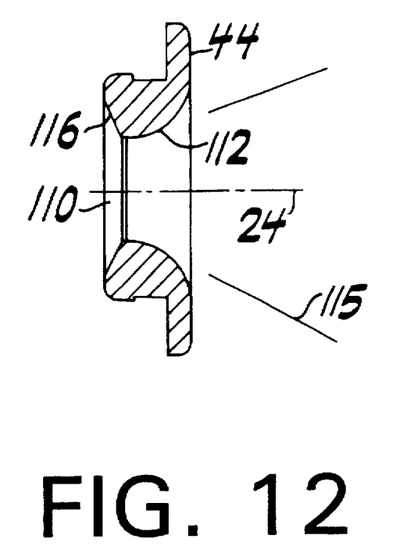
FIG. 12 is an isolated view of a portion of FIG. 5 showing a seal reinforcing member.
Figure 13:
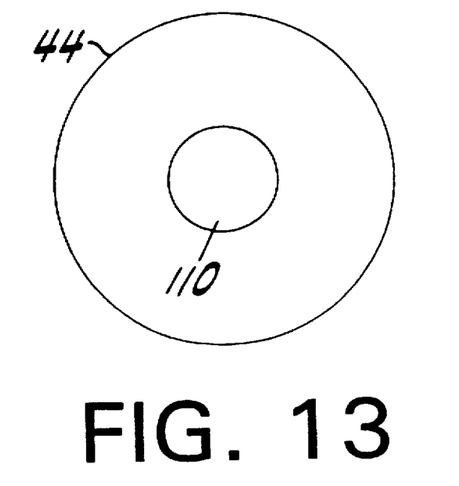
FIG. 13 is a right side view of FIG. 12.
Figure 14:
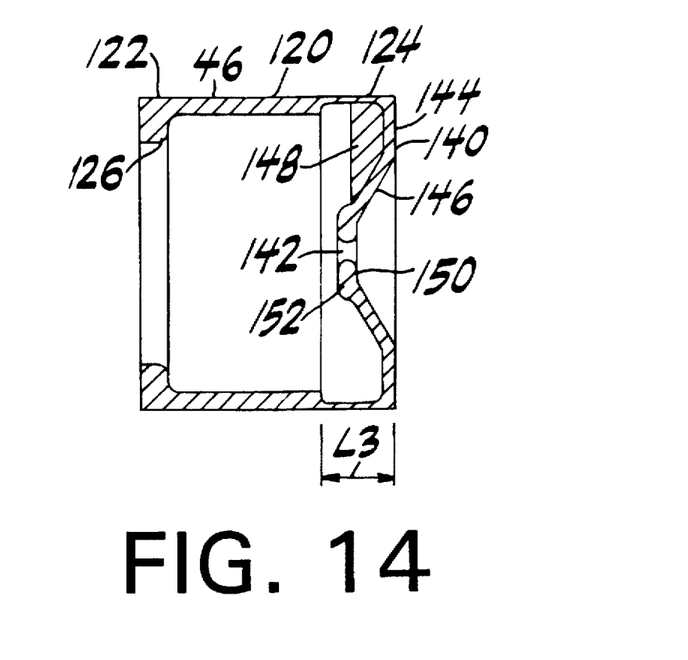
FIG. 14 is an isolated view of a portion of FIG. 5 showing the proximal seal member of the present invention.
Figure 15:
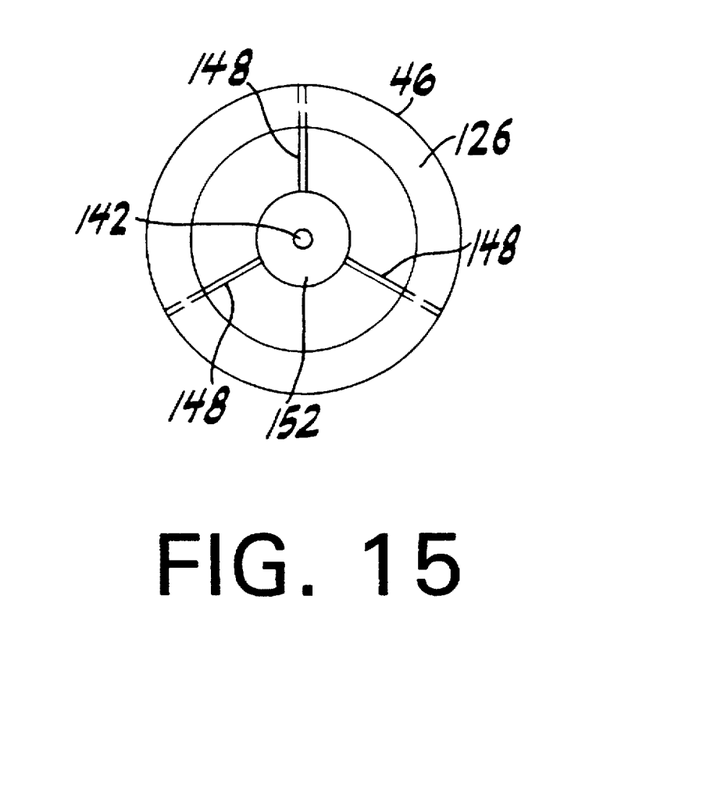
FIG. 15 is a left side elevational view of FIG. 14.

Reinforcing member 56 has a generally quarter-circle cross-section as best seen in FIGS. 9 and 10. The quarter-circle profile is, however, modified slightly by the deletion of material necessary to form the lead-in proximal and distal surfaces and associated conical wall sections as best seen in FIG. 11. The combination of the quarter-circle profile and material deletion produces a primary reinforcing member 56 having along its perimeter a somewhat bulbous cross-sectional appearance. Thus, as best seen in FIG. 11, when viewed in a plane perpendicular to planar surfaces 74 and 78, this cross-section causes member 56 to have a thickness T along a line perpendicular to a transverse midline through surfaces 74 and 78, this thickness decreasing proximally and distally relative to this midline. The cross-sectional shape of reinforcing member 56 enhances the frictional engagement between the slit and an instrument inserted therethrough and also aids in urging the opposing slit edges 70, 72 together when there is no instrument in the cannula. Lateral reinforcing members 58 and 60 supplement the reinforcing action of member 56 by having outer arcuate surfaces 90 and 92, respectively, which contact the inner surface of housing 30 to further compress the edges of the slit. Members 58 and 60 are longitudinally coextensive with member 56. In the preferred embodiment, members 56, 58 and 60 extend distally to a point on the order of 0.238 inches (6.05 mm) from floor 81. The arcuate surfaces 90, 92 are situated at a diameter D4 which is on the order of 0.77 inches (19.56 mm), greater than diameter D2 so they may act on members 58 and 60 to pre-load slit 54 with a predetermined amount of closure force when no instrument is present.

Distal seal 42 is designed to fit within the interior of housing 30 which is provided with a cylindrical wall 94, an adjacent annular groove 96 and a cylindrical proximal annular rib 98. Annular rib 50 and annular groove 52 of seal 42 are designed to mate, respectively, with annular groove 96 and annular rib 98 of housing 30. Arcuate wall sections 90 and 92 of the valve body are designed to contiguously engage opposing portions of cylindrical wall 94 in order to provide lateral resistance to reinforcing members 58 and 60. In the preferred embodiment, to facilitate manufacture and assembly, the proximal end 30a of housing 30 may be separately molded from the distal end 30b (which may be part of body 12).

Figure 4:
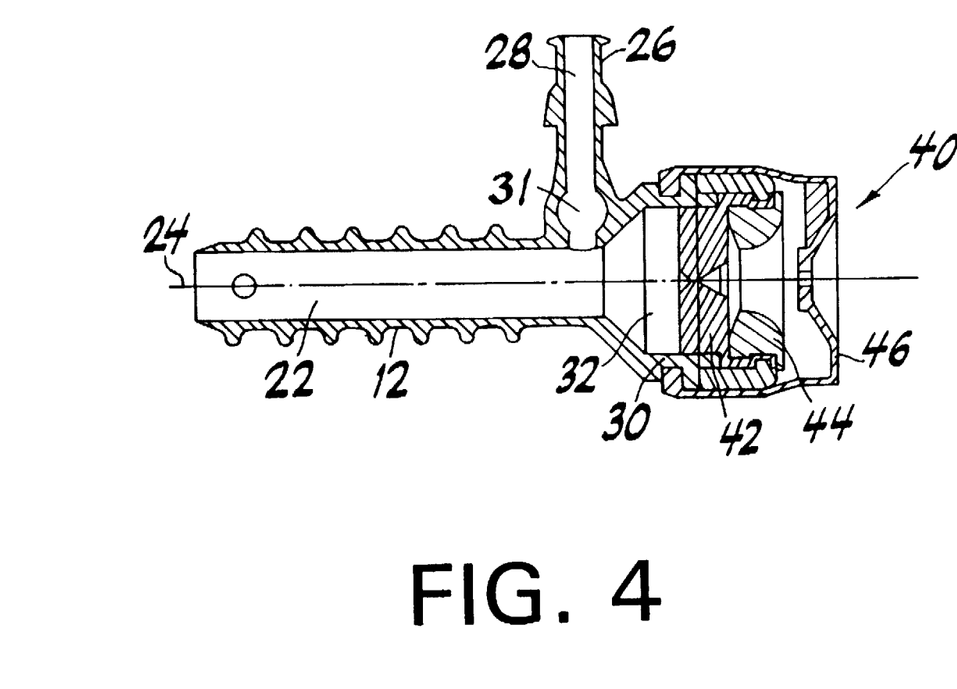
FIG. 4 is a cross-sectional view of FIG. 1 omitting the valve stem for clarity.
Figure 5:
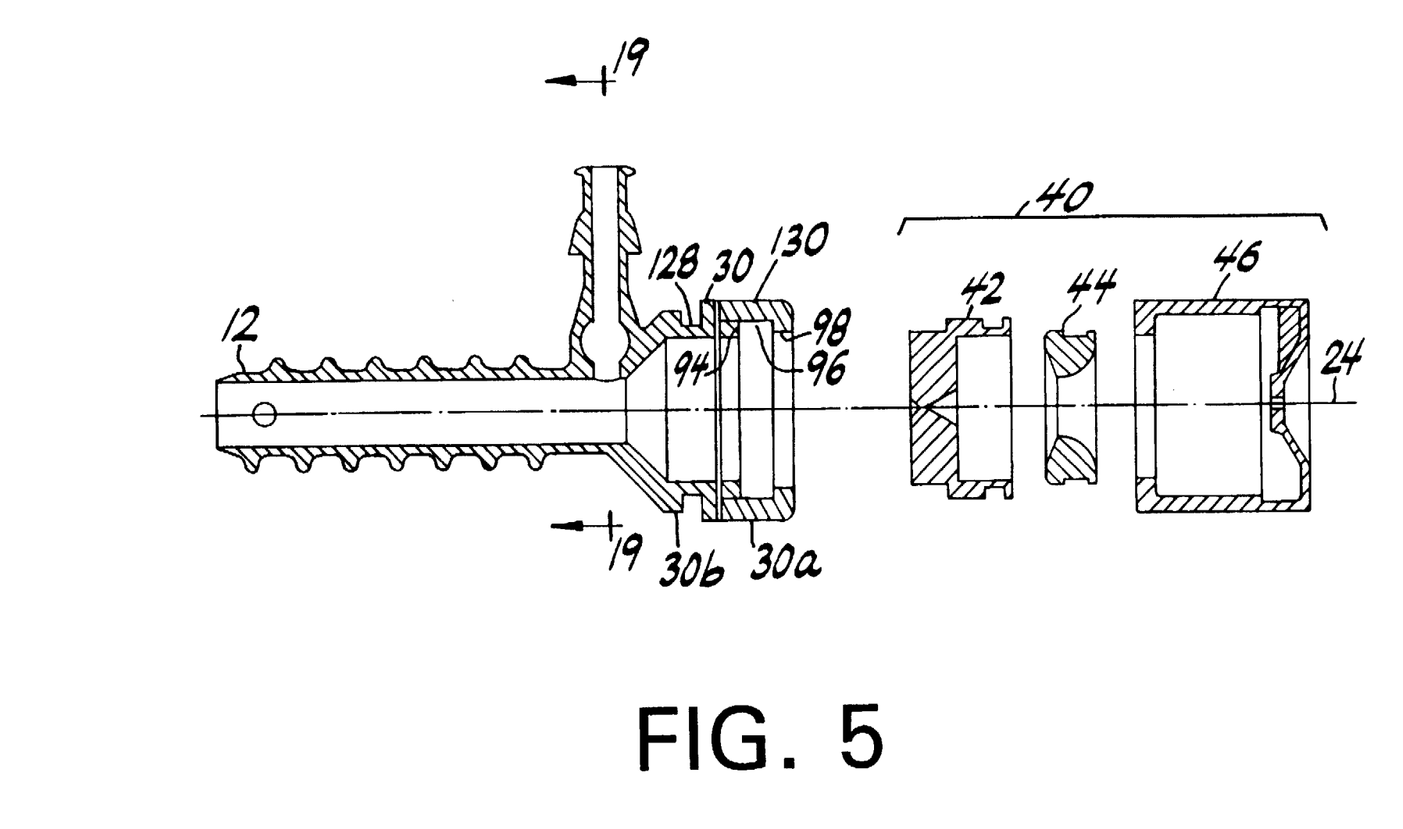
FIG. 5 is an exploded view of FIG. 4.
Figure 16A:
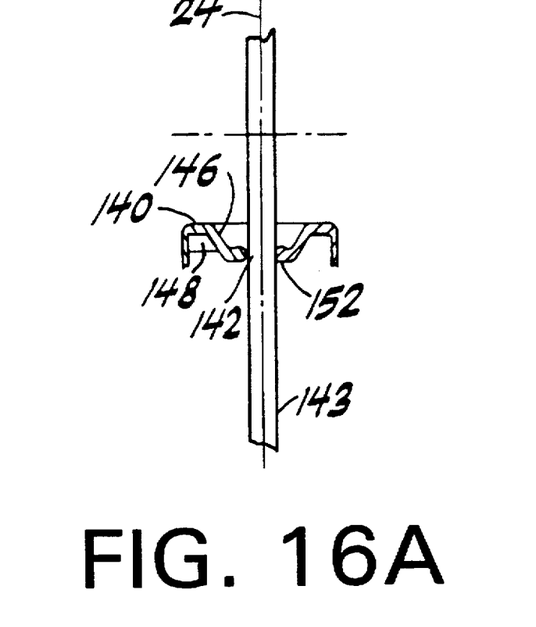
FIGS. 16a and 16b are schematic representations of the operation of the proximal seal member with an instrument shaft in position.
Figure 16B:
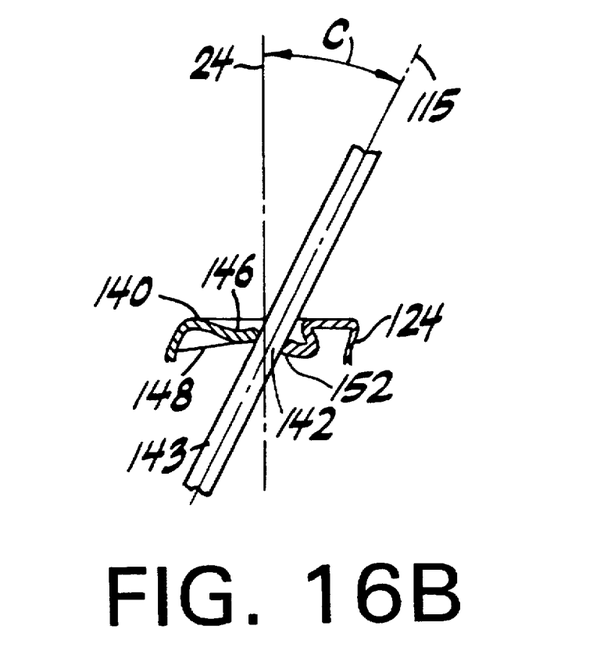

Reinforcing and limitation member 44 has an annular body provided with a central clearance aperture 110. In the preferred embodiment, member 44 is formed from a rigid plastic material in order to fit within the interior area 83 of valve member 42 to secure it within the housing. The diameter and rigidity of member 44 are such that, when assembled as shown in FIG. 4, it will cause valve member 42 to be pressed against annular rib 98. Member 44 serves as a size limiter, since its central aperture 110 is fixed in size and, in combination with proximal seal member 46, it also serves to limit the angle at which instruments may be inserted into the cannula. Annular surface 112 limits the angular deviation of an elongated instrument inserted along axis 24 to a range within which circular apertures 142 of the proximal seal 46 may move laterally without being distorted out of its circular shape. This maintains seal integrity within a range of angular deviations. This range may be represented by an imaginary cone having its axis aligned with axis 24 and having a conical surface 115 (not shown to scale). As shown in FIG. 16b, an instrument may be inserted through clearance aperture 110 anywhere within conical surface 115 without stretching aperture 142 out of shape. In the preferred embodiment, member 44 is molded from a relatively rigid biocompatible material and the diameter of central aperture 110 may be on the order of 0.323 inches (8.2 mm) when slit length L2 is 0.3 inches (7.62 mm). The proximally facing, annular surface 112 has a radius of curvature on the order of 0.188 inches (4.78 mm). This surface permits a limited amount of axial movement of the proximal outer seal 46 as will be understood below. The distally facing, annular surface 116 is tapered to permit the floor 81 of distal seal 42 to move axially within chamber 32 as may be necessary when an instrument is withdrawn from the cannula 10.

Outer, proximal seal member 46 comprises an elastomeric body adapted to fit on the exterior of housing 30. In the preferred embodiment, with a cylindrical housing, seal 46 has a cylindrical wall 120 having a distal annular section 122 and a proximal annular section 124. An annular radially inwardly extending rib 126 is provided at the distal end of wall 122 and adapted to engage annular groove 128 in the exterior surface of housing 30. The interior surface of wall section 122 is sized to frictionally engage the exterior cylindrical surface 130 of housing 30. Wall section 124 has a predetermined longitudinal length L3 and supports at its proximal end a transverse end wall section 140 having an axially aligned circular aperture 142 surrounded by a flat annular transverse wall section 150. End wall 140 has an outer, flat annular transverse section 144 and an adjacent inner conical section 146 interposed between transverse sections 144 and 150. Three equilaterally spaced support ribs 148 join annular wall 124 to transverse wall section 144 and conical wall section 146. The function of end wall 140 is to minimize any detrimental effects of eversion and to provide a floating circular seal for preventing leakage of fluid along the shafts of elongated instruments inserted through the cannula.

The anti-eversion feature of wall 140 facilitates maintaining the wall ready to receive an instrument. Eversion of seals engaging an instrument shaft may sometimes occur on instrument withdrawal. Thus, the frictional contact between an instrument shaft and circular aperture 142 may cause the latter to be momentarily moved to the proximal side of end wall 140 (e.g. by eversion of conical section 146). Ribs 148 would then be stretched and tend to return aperture 142 to its proper position.

The floating feature is provided by the conical wall section 146 and by the relatively thin wall section 124 which extends a predetermined distance away from the proximal end of the cannula housing so as to space end wall 140 from the housing. As best seen in FIGS. 16a and 16b, the axial length and thinness of wall section 124 enables it to flex laterally in response to forces exerted by an instrument shaft 143 on aperture 142 and conical wall section 146. The sealing function of aperture 142 itself is enhanced by conical wall section 146 and by reinforcing wall section 152 which surrounds aperture 142. The reinforcing section 152 has a thickness greater than that of the adjacent conical wall section 146 in order to assure contact with an instrument shaft as it is inclined at an angle C. Thus, the conical wall section, being relatively thin is able to flex to enable section 152 to be moved to a tilted or inclined position (FIG. 16b) relative to a transverse plane (i.e. the plane of aperture 142 in FIG. 16a in an unbiased mode perpendicular to axis 24 with an instrument present and axially aligned). In one preferred embodiment, the proximal seal 46 is molded from a biocompatible elastomeric material similar to that used to form distal seal 42 and the overall axial length of seal member 46 is 0.856 inches (21.74 mm) while the length of thin section 124 is 0.240 inches (6.10 mm). The diameter of member 46 is 1.050 inches (26.67 mm) and the diameter of circular aperture 142 is 0.070 inches (1.78 mm). The thickness of distal wall section 122 may be on the order of 0.064 inches (1.63 mm) while that of the proximal wall section may be on the order of 0.020 inches (0.51 mm) although these dimensions may vary given different materials. It will be understood that the proximal seal member 46 must flex a certain amount in order to achieve its intended functions. If such flexibility is not available from the choice of elastomeric materials used, then minor variations in structure may be employed, some examples of which are shown below.

As shown in FIGS. 16a and 16b, an instrument shaft inserted axially through aperture 142 will be frictionally engaged by the surrounding annular reinforcing wall section 152. As the instrument shaft is inclined relative to axis 24, as shown in FIG. 16b the frictional engagement between the shaft and wall section 152 will be maintained through an angle C. Radial ribs 148 will stretch accordingly as will annular wall section 124 and conical wall section 146 in order to accommodate deflection of the instrument shaft within a certain predetermined range.

Figure 17A:
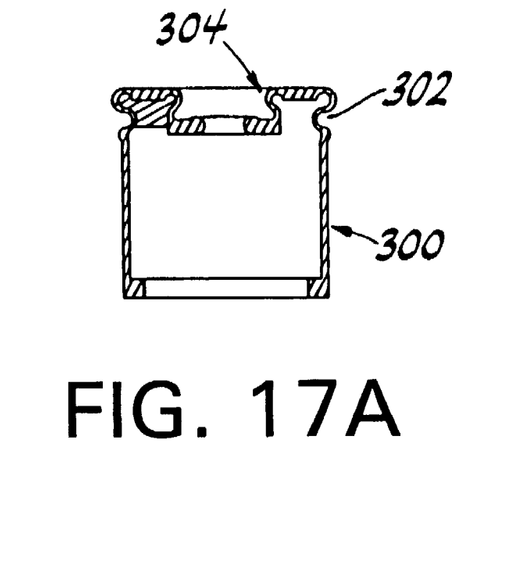
FIGS. 17a and 17b are schematic representations of alternate embodiments of the proximal seal member of the invention.
Figure 17B:
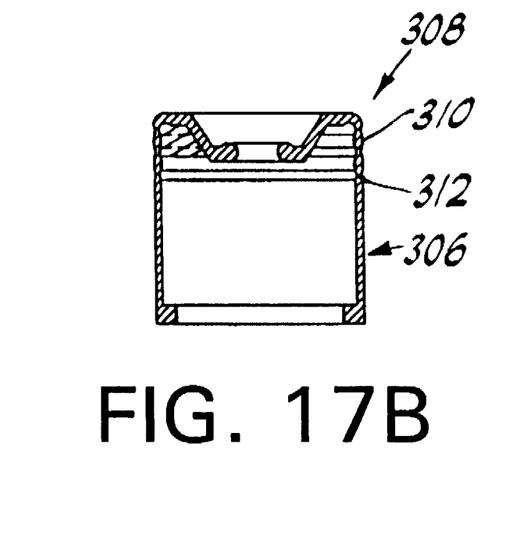
Figure 18A:
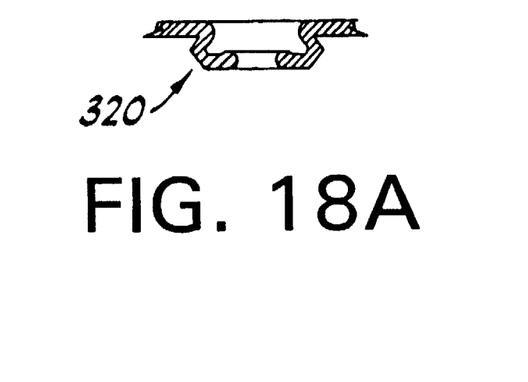
FIGS. 18a and 18b are schematic representations of alternate embodiments of the conical wall section of the proximal seal member.
Figure 18B:
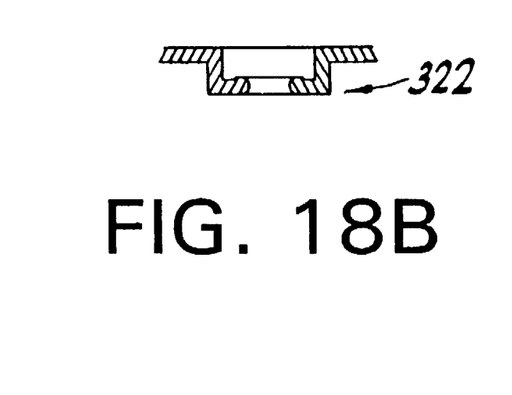

It will be understood that the floating, sealing nature of end wall 140 may be provided in a variety of ways. As shown in FIGS. 17a and 17b and FIGS. 18a and 18b, the floating aspect of end wall 140 may be achieved by structures other than those shown above. Referring to FIG. 17a, proximal seal 46 may be made in the form of proximal seal 300 having a cylindrical serpentine wall section 302 and a conical serpentine section 304, all other portions of seal 300 being essentially the same as corresponding portions of seal 46. Similarly in FIG. 17b, proximal seal 306 has a ribbed cylindrical wall 308 having annular ribs 310 and grooves 312. FIGS. 18a and 18b depict two possible variations of conical wall section 146 in the form of multi-faceted conical wall section 320 and cylindrical wall section 322.

Figure 19:
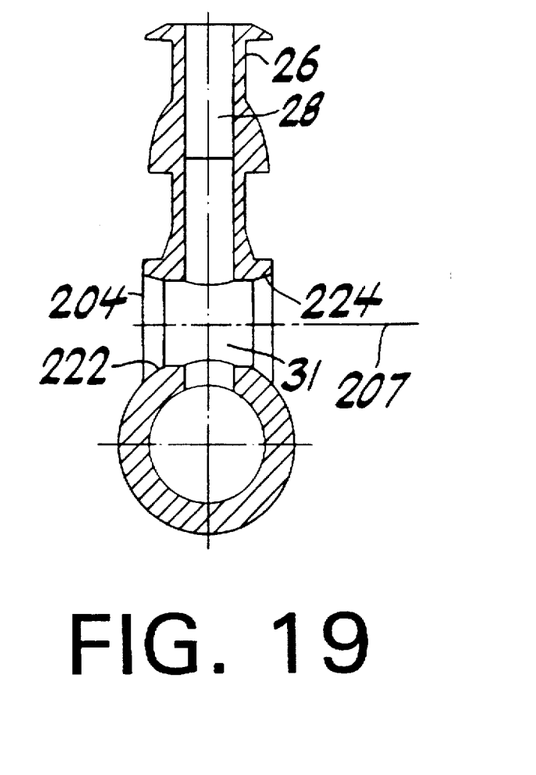
FIG. 19 is a cross-sectional view of FIG. 5 taken along the line 19—19.
Figure 20:
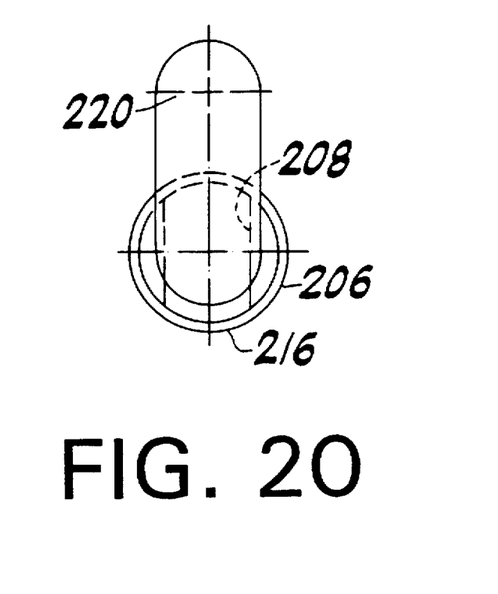
FIG. 20 is a side elevational view of a portion of FIG. 3 showing only the valve stem.

The elastomeric stopcock valve 200 used in the cannula of FIGS. 1–4 is best seen in FIGS. 1, 3, 19 and 20. Valve 200 comprises a valve stem 202 and a valve seat 204. Stem 202 is formed entirely of an elastomeric material such as polyurethane having a Shore hardness number on the order of 40–80 (A scale) and comprises a shaft 206 having an axis 207, a transverse throughbore 208 and opposing ends 210 and 212 provided with annular ribs 214 and 216 extending radially outwardly from shaft 206. A handle 220 is integrally formed at the proximal end of shaft 206 and extends transversely in a conventional manner to enable shaft 206 to be rotated about its axis 207. Valve stem 202 is sized to fit within transverse valve seat 204 which, as best seen in FIG. 19, is an opening formed in transverse recess 31 and aligned along axis 207. Annular countersink rims 222 and 224 at the opposite ends of valve seat 204 are tapered outwardly and adapted to engage ribs 214 and 216, respectively. Throughbore 208 may be aligned with channel 28 or turned transversely to close the valve. The elastomeric nature of the valve stem 202 produces a simple valve design which enables the stopcock valve to operate efficiently with minimal complexity.

It will be understood by those skilled in the art that numerous improvements and modifications may be made to the preferred embodiments of the invention disclosed herein without departing from the spirit and scope thereof.

What is claimed is:

1. A sealing cannula for enabling passage of elongated instruments therethrough comprising:
    a tubular housing having an axis, an inner surface and outer surface, a distal end, a proximal end and an axially aligned tubular body extending distally from said distal end;
    a first proximal elastomeric seal comprising:
        a first tubular wall having a proximal end and a distal end;
        a first transverse end wall at the proximal end of said first tubular wall, said first transverse end wall comprising an expandable circular aperture; and
        floating means for enabling lateral and inclined motion of said circular aperture relative to said axis when an elongated instrument is inserted therethrough;
        means for securing said first tubular wall to said housing, aligning said circular aperture along said axis and spacing said circular aperture a first predetermined longitudinal distance from said proximal end of said housing;
    a second distal elastomeric seal comprising:
        a second tubular wall having a proximal end and a distal end;
        a second transverse end wall at the distal end of said second tubular wall, said second transverse end wall having proximal and distal sides and a transversely oriented linear slit therethrough;
        means for securing said second tubular wall within said housing, aligning said slit along said axis and spacing said slit a second predetermined longitudinal distance from said circular aperture; and
        a generally rectangular primary reinforcing member formed about said slit, and extending distally a predetermined distance from said second transverse end wall on the distally facing side of said end wall.

2. A sealing cannula according to claim 1 further comprising a pair of proximally facing, axially transverse, lead-in planar surfaces bounding said proximal side of said slit and a pair of distally facing, axially transverse lead-in planar surfaces bounding said distal side of said slit.

3. A sealing cannula according to claim 2 further comprising a first pair of opposing conical wall sections joining adjacent ends of said proximally facing planar surfaces and a second pair of opposing conical wall sections joining adjacent ends of said distally facing planar surfaces.

4. A sealing cannula according to claim 1 further comprising a pair of transversely oriented opposing secondary reinforcing members abutting said reinforcing member on opposite lateral sides of said slit, said secondary reinforcing members comprising a radially outer surface for engaging the inner surface of said housing.

5. A sealing cannula according to claim 2 wherein said distally facing lead-in planar surfaces terminate in a peripheral distal-most edge and wherein the distally facing side of said reinforcing member is curved proximally and outwardly from said distal-most edge.

6. A sealing cannula according to claim 1 wherein said floating means comprises an annular wall section formed at said proximal end of said first tubular wall, said annular wall section having a predetermined thickness adapted to enable said first transverse end wall to move relative to said axis, said annular wall section further having a predetermined length to enable said first transverse end wall to be spaced said predetermined longitudinal distance from said housing.

7. A sealing cannula according to claim 1 wherein said first tubular wall is adapted to engage the outer surface of said housing, further comprising an annular rib at said distal end of said first tubular wall for engaging an annular groove on said outer surface of said housing.

8. A sealing cannula according to claim 1 wherein said floating means comprises a distally tapered conical wall section surrounding said circular aperture and further comprising resilient means secured to said first transverse end wall for enabling proximal, everting motion of said conical wall section upon removal of an instrument therefrom and for returning said first conical wall section to its distally tapered configuration after said instrument is disengaged from said circular aperture.

9. A sealing cannula according to claim 8 wherein said resilient means comprises a plurality of radially extending reinforcing ribs joining said first transverse end wall, said conical wall section and said first tubular wall.

10. A sealing cannula according to claim 9 wherein each of said radially extending ribs further comprise a flat planar body.

11. A sealing cannula according to claim 1 further comprising a limitation means interposed between said first and second elastomeric seals for limiting the angular deviation of an elongated instrument from said cannula axis to a range between a first direction aligned with said cannula axis and a second direction lying on the conical surface of an imaginary cone having its axis aligned with said cannula axis and having a predetermined apex angle about said cannula axis.

12. A sealing cannula according to claim 11 wherein said limitation means comprises an annular member having an axially aligned clearance aperture for receiving an instrument shaft therethrough, said clearance aperture surrounded by a radially outwardly and proximally extending annular surface having a predetermined arcuate profile in an axial plane.

13. A sealing cannula for providing a passageway for enabling passage of elongated instruments therethrough from an ambient, non-fluid filled area into a fluid filled surgical field while sealingly separating one portion of the cannula from the other comprising:

a hollow cylindrical housing having an axis, a distal end, a proximal end and an axially aligned tubular body extending distally from said distal end;

a first proximal sealing cap means for preventing fluid transmission from said housing when an instrument shaft is inserted therethrough comprising:

a first cylindrical elastomeric wall having an axis, a proximal end and a distal end, said distal end having a first predetermined thickness over a predetermined distal axial length portion thereof and said proximal end having a second predetermined thickness over a predetermined proximal axial length portion thereof, said predetermined first thickness greater than said predetermined second thickness;

a first transverse end wall enclosing the proximal end of said first cylindrical wall, said end wall comprising an axially aligned circular aperture;

means for spacing said first end wall a predetermined longitudinal distance from said proximal end of said housing;

a second distal seal comprising:

a second cylindrical wall having a proximal end and a distal end;

a second end wall enclosing the distal end of said second cylindrical wall, said second end wall having a transverse linear slit therethrough; and a generally rectangular reinforcing member formed in said end wall about said slit and extending distally a predetermined distance from said end wall on the distally facing side of said end wall, said slit bounded by a pair of proximally and distally facing, lead-in linear surfaces.

14. A sealing cannula according to claim 13 wherein said proximally and distally facing lead-in linear surfaces are each joined at their adjacent ends by respective conical wall sections.

15. A sealing cannula according to claim 13 wherein said proximally and distally facing lead-in linear surfaces are oriented relative to each other at angles between approximately 60° and 90°.

16. A sealing cannula according to claim 13 wherein said means for spacing said first end wall comprises lateral motion enabling means for enabling said circular aperture to be laterally movable relative to said axis, said lateral-motion enabling means comprising:

a unitary cylindrical body having a proximal wall section and a distal wall section, said proximal wall section having a first predetermined rigidity and said distal wall section having a second predetermined rigidity, said first predetermined rigidity being less than said second predetermined rigidity, said proximal and distal wall sections adapted for lateral movement relative to each other; and attachment means for releasably attaching said distal wall section to said housing so as to hold said first end wall spaced from the proximal end of said housing to permit lateral movement therebetween.

17. A method for sealing a cannula which provides a passageway for elongated surgical instruments to pass therethrough from an ambient non-fluid filled area to a fluid filled surgical work site, the method comprising the steps of:

providing an elongated cannula body having a tubular passageway having a proximal end and a distal end;

providing at the proximal end of the tubular passageway a distal seal means for sealing the work site from ambient when no instrument is present in the cannula;

providing proximally of said distal seal means a proximal circular aperture seal means for sealingly engaging an instrument shaft of an instrument inserted through the cannula;

providing a floating means associated with said proximal circular aperture seal means for enabling said proximal circular aperture seal means to move in a lateral and inclined direction relative to the axis of said cannula to maintain engagement between said proximal circular aperture seal means and the instrument shaft within a predetermined range of misalignment of the axis of the instrument shaft with the axis of the cannula.

18. A method according to claim 17 wherein said step of providing a floating means comprises the steps of:

providing in said proximal circular aperture seal means an expandable, circular aperture and aligning the axis of said circular aperture with the axis of the cannula;

interposing between said distal seal means and said proximal circular aperture seal means an annular cylindrical wall section having a predetermined axial length; and attaching said expandable circular aperture to said annular cylindrical wall section at a position spaced a predetermined axial distance from said proximal end of said tubular passageway.

19. A method according to claim 18 further comprising the step of interposing, between said distal seal means and said circular aperture seal means, a limitation means for limiting the angular deviation of an elongated instrument from said cannula axis to a range between a first direction aligned with said cannula axis and a second direction lying on the conical surface of an imaginary cone having its axis aligned with said cannula axis and having a predetermined apex angle about said cannula axis.

20. A method according to claim 19 wherein said limitation means comprises an axially aligned clearance aperture for receiving an instrument shaft therethrough, said clearance aperture surrounded by a radially outwardly and proximally extending annular surface having a predetermined arcuate profile in an axial plane.

\* \* \* \* \*